US012065484B2

(12) United States Patent
Kalergis Parra et al.

(10) Patent No.: US 12,065,484 B2
(45) Date of Patent: Aug. 20, 2024

(54) SPECIFIC MONOCLONAL ANTIBODY AGAINST THE N ANTIGEN OF HUMAN RESPIRATORY SYNCYTIAL VIRUS (hRSV) USEFUL FOR TREATING INFECTION, DETECTION THEREOF AND DIAGNOSIS

(71) Applicants: PONTIFICIA UNIVERSIDAD CATOLICA DE CHILE, Santiago (CL); FUNDACION COPEC UNIVERSIDAD CATÓLICA, Santiago (CL)

(72) Inventors: Alexis Kalergis Parra, Santiago (CL); Susan Bueno Ramírez, Santiago (CL)

( * ) Notice: Subject to any disclaimer, the term of this patent is extended or adjusted under 35 U.S.C. 154(b) by 765 days.

(21) Appl. No.: 17/273,172

(22) PCT Filed: Sep. 3, 2018

(86) PCT No.: PCT/CL2018/050079
§ 371 (c)(1),
(2) Date: Mar. 3, 2021

(87) PCT Pub. No.: WO2020/047683
PCT Pub. Date: Mar. 12, 2020

(65) Prior Publication Data

US 2021/0347862 A1 Nov. 11, 2021

(51) Int. Cl.

*A61P 31/14* (2006.01)
*C07K 16/10* (2006.01)
*G01N 33/543* (2006.01)
*G01N 33/569* (2006.01)
*G01N 33/58* (2006.01)
*G01N 33/60* (2006.01)

(52) U.S. Cl.

CPC .......... *C07K 16/1027* (2013.01); *A61P 31/14* (2018.01); *G01N 33/543* (2013.01); *G01N 33/56983* (2013.01); *G01N 33/581* (2013.01); *G01N 33/582* (2013.01); *G01N 33/60* (2013.01); *C07K 2317/24* (2013.01); *C07K 2317/565* (2013.01); *G01N 2333/135* (2013.01)

(58) Field of Classification Search

CPC ............ C07K 16/1027; C07K 2317/24; C07K 2317/565; A61P 31/14; G01N 33/543; G01N 33/56983; G01N 33/581; G01N 33/582; G01N 33/60; G01N 2333/135; A61K 2039/505
See application file for complete search history.

(56) References Cited

U.S. PATENT DOCUMENTS

2002/0081573 A1 6/2002 Lassen et al.

FOREIGN PATENT DOCUMENTS

CN 101130765 2/2008
WO 2013/076702 5/2013

OTHER PUBLICATIONS

Dondelinger et al. Understanding the Significance and Implications of Antibody Numbering and Antigen-Binding Surface/ Residue Definition. Frontiers in Immunology. 2018, 9:2278) (Year: 2018).*
Lin et al. Improved affinity of a chicken single-chain antibody to avian infectious bronchitis virus by site-directed mutagenesis of complementarity-determining region H3. African Journal of Biotechnology. 2011, 10(79):18294-18302. (Year: 2011).*
Zhu et al. A highly potent extended half-life antibody as a potential RSV vaccine surrogate for all infants. Sci Transl Med. 2017, 9(388): eaaj1928. (Year: 2017).*
Mazur et al. The respiratory syncytial virus vaccine landscape: lessons from the graveyard and promising candidates. Lancet Infect Dis. 2018, 18: e295-311. (Year: 2018).*
Terrosi et al. Immunological Characterization of Respiratory Syncytial Virus N Protein Epitopes Recognized by Human Cytotoxic T Lymphocytes. 2007. Viral Immunology, 20(3): 399-406. (Year: 2007).*
Cespedes et al. Surface expression of the hRSV nucleoprotein impairs immunological synapse formation with T cells. 2014. PNAS, 111(31): E3214-E3223. (Year: 2014).*
Taleb et al. Human respiratory syncytial virus: pathogenesis, immune responses, and current vaccine approaches. 2018. Eur J Clin Microbiol Infect Dis, 37: 1817-1827. (Year: 2018).*
Gomez, et al., "Respriatory Syncytial Virus Detection in Cells and Clinical Samples by using Three New Monoclonal Antibodies", Journal of Medical Virology, vol. 86, No. 7, 2014, pp. 1256-1266.
Murray, et al., "Characterization of Monoclonal Antibodies Raised against Recombinant Respiratory Syncytial Virus Nucleocapsid (N)Protein: Identification of a Region in the Carboxy Terminus of N Involved in the Interaction with P Protein", Virology, vol. 289, No. 2, 2001, pp. 252-261.
Kumari, et al., "Development of a Luciferase Immunoprecipitation System Assay to Detect IgG Antibodies against Human Respiratory Syncytial Virus Nucleoprotein", Clinical and Vaccine Immunology, vol. 21, No. 3, Mar. 2014, pp. 383-390.

(Continued)

*Primary Examiner* — Brad Duffy
*Assistant Examiner* — Amber K Faust
(74) *Attorney, Agent, or Firm* — HSML P.C.

(57) ABSTRACT

The invention relates to a monoclonal antibody or fragment thereof, which recognizes the N (nucleocapsid) protein of the human respiratory syncytial virus (RSV), useful for the development of diagnostic methods for RSV infection and for the production of pharmaceutical compositions intended for the treatment, protection and/or prophylaxis of RSV infection.

12 Claims, 4 Drawing Sheets

Specification includes a Sequence Listing.

(56) References Cited

OTHER PUBLICATIONS

Rey-Jurado, et al., "Immunological Features of Respiratory Syncytial Virus-Caused Pneumonia-Implications for Vaccine Design", International Journal of Molecular Sciences, vol. 18, No. 3, 556, 2017, 19 pages.
International Search Report issued in International Application No. PCT/JP2018/050079, Feb. 12, 2019, 9 pages.

* cited by examiner

A.

B.

SEQUENCE LISTING

```
<160> NUMBER OF SEQ ID NOS: 16

<210> SEQ ID NO 1
<211> LENGTH: 155
<212> TYPE: PRT
<213> ORGANISM: Murine

<400> SEQUENCE: 1

Trp Glu Phe Met Glu Trp Thr Trp Val Phe Leu Phe Leu Met Ala Val
1               5                   10                  15

Val Thr Gly Val Ser Glu Val Gln Leu Gln Gln Ser Gly Thr Glu Leu
            20                  25                  30

Val Lys Pro Gly Ala Ser Val Lys Leu Ser Cys Thr Ala Ser Gly Phe
        35                  40                  45

Asn Ile Lys Asp Ala Tyr Ile His Trp Met Arg Gln Arg Pro Glu Gln
    50                  55                  60

Gly Leu Glu Trp Leu Gly Arg Ile Asp Pro Ala Asn Gly Asn Ser Lys
65                  70                  75                  80

Tyr Asp Pro Phe Gln Gly Lys Ala Thr Ile Thr Ala Asp Thr Ser Ser
                85                  90                  95

Asn Thr Ala Tyr Leu Gln Leu Ser Ser Leu Thr Ser Glu Asp Thr Ala
            100                 105                 110

Val Tyr Tyr Cys Ala Ser Gly Phe Tyr Leu Arg Thr Met Asp Tyr Trp
        115                 120                 125

Gly Gln Gly Thr Ser Val Thr Val Ser Ser Ala Lys Thr Thr Ala Pro
    130                 135                 140

Ser Val Tyr Pro Leu Ala Pro Gly Ser Leu Gly
145                 150                 155


<210> SEQ ID NO 2
<211> LENGTH: 151
<212> TYPE: PRT
<213> ORGANISM: Murine
```

<400> SEQUENCE: 2

```
Phe Leu Val Asp Met Glu Ser Asp Thr Leu Leu Leu Trp Val Leu Leu
1               5                   10                  15

Leu Trp Val Pro Gly Ser Thr Gly Asp Ile Val Leu Thr Gln Ser Pro
            20                  25                  30

Ala Ser Leu Ala Val Ser Leu Gly Gln Arg Ala Thr Ile Ser Tyr Arg
        35                  40                  45

Ala Ser Lys Ser Val Ser Thr Ser Gly Tyr Ser Tyr Met His Trp Asn
    50                  55                  60

Gln Gln Lys Pro Gly Gln Pro Pro Arg Leu Leu Ile Tyr Leu Val Ser
65                  70                  75                  80

Asn Leu Glu Ser Gly Val Pro Ala Arg Phe Ser Gly Ser Gly Ser Gly
                85                  90                  95

Thr Asp Phe Thr Leu Asn Ile His Pro Val Glu Glu Glu Asp Ala Ala
            100                 105                 110

Thr Tyr Tyr Cys Gln His Ile Arg Glu Leu Thr Arg Ser Glu Gly Gly
        115                 120                 125

Pro Ser Trp Lys Asn Gly Leu Met Leu His Gln Leu Tyr Pro Ser Ser
    130                 135                 140

His His Pro Val Ser Leu Gly
145                 150
```

<210> SEQ ID NO 3
<211> LENGTH: 473
<212> TYPE: DNA
<213> ORGANISM: Murine

<400> SEQUENCE: 3

```
ttgggaattc atggaatgga cctgggtttt tctcttcctg atggcagtgg ttacaggggt      60

caattcagag gttcaactgc agcagtctgg gacagaactt gtgaagccag gggcctcagt     120

caaattgtcc tgcacagctt ctggcttcaa cattaaagac gcctatattc actggatgag     180

gcagaggcct gaacagggcc tggagtggct tgggaggatt gatcctgcga atggtaattc     240

taaatatgac ccgaagttcc agggcaaggc cactataaca gcagacacat cctccaacac     300

agcctacctg caactcagca gcctgacatc tgaggacact gccgtctatt actgtgcgag     360

cggcttctac ttgaggacta tggactactg gggtcaagga acctcagtca ccgtctcctc     420

agccaaaaca acagccccat ccgtttatcc cttggcccct ggaagcttgg gaa            473
```

<210> SEQ ID NO 4
<211> LENGTH: 460
<212> TYPE: DNA
<213> ORGANISM: Murine

<400> SEQUENCE: 4

```
tttttctagt cgacatggag tcagacacac tgctgttatg ggtactgctg ctctgggttc      60

caggttccac tggtgacatt gtgctgacac agtctcctgc ttccttagct gtatctctgg     120

ggcagagggc caccatctca tacagggcca gcaaaagtgt cagtacatct ggctatagtt     180

atatgcactg gaaccaacag aaaccaggac agccacccag actcctcatc tatcttgtat     240

ccaacctaga atctggggtc cctgccaggt tcagtggcag tgggtctggg acagacttca     300

ccctcaacat ccatcctgtg gaggaggagg atgctgcaac ctattactgt cagcacatta     360

gggagcttac acgttcggag gggggaccaa gctggaaata aaacgggctg atgctgcacc     420

aactgtatcc atcttcccac catccagtaa gcttgggaaa                           460
```

<210> SEQ ID NO 5
<211> LENGTH: 8
<212> TYPE: PRT
<213> ORGANISM: Murine

<400> SEQUENCE: 5

```
Gly Phe Asn Ile Lys Asp Ala Tyr
1               5
```

<210> SEQ ID NO 6
<211> LENGTH: 8
<212> TYPE: PRT
<213> ORGANISM: Murine

<400> SEQUENCE: 6

```
Ile Asp Pro Ala Asn Gly Asn Ser
1               5
```

<210> SEQ ID NO 7
<211> LENGTH: 11
<212> TYPE: PRT
<213> ORGANISM: Murine

<400> SEQUENCE: 7

```
Ala Ser Gly Phe Tyr Leu Arg Thr Met Asp Tyr
1               5                   10
```

<210> SEQ ID NO 8
<211> LENGTH: 24
<212> TYPE: DNA
<213> ORGANISM: Murine

<400> SEQUENCE: 8

```
ggcttcaaca ttaaagacgc ctat                                            24
```

<210> SEQ ID NO 9
<211> LENGTH: 24
<212> TYPE: DNA
<213> ORGANISM: MURINE

<400> SEQUENCE: 9

```
attgatcctg cgaatggtaa ttct                                            24
```

<210> SEQ ID NO 10
<211> LENGTH: 33
<212> TYPE: DNA
<213> ORGANISM: MURINE

<400> SEQUENCE: 10

```
gcgagcggct tctacttgag gactatggac tac                                  33
```

<210> SEQ ID NO 11
<211> LENGTH: 10
<212> TYPE: PRT
<213> ORGANISM: MURINE

<400> SEQUENCE: 11

```
Lys Ser Val Ser Thr Ser Gly Tyr Ser Tyr
1               5                   10
```

<210> SEQ ID NO 12
<211> LENGTH: 4
<212> TYPE: PRT

-continued

```
<213> ORGANISM: MURINE

<400> SEQUENCE: 12

Leu Val Ser Asn
1


<210> SEQ ID NO 13
<211> LENGTH: 8
<212> TYPE: PRT
<213> ORGANISM: MURINE

<400> SEQUENCE: 13

Gln His Ile Arg Glu Leu Thr Arg
1               5


<210> SEQ ID NO 14
<211> LENGTH: 30
<212> TYPE: DNA
<213> ORGANISM: MURINE

<400> SEQUENCE: 14

aaaagtgtca gtacatctgg ctatagttat                                      30


<210> SEQ ID NO 15
<211> LENGTH: 12
<212> TYPE: DNA
<213> ORGANISM: MURINE

<400> SEQUENCE: 15

cttgtatcca ac                                                         12


<210> SEQ ID NO 16
<211> LENGTH: 24
<212> TYPE: DNA
<213> ORGANISM: MURINE

<400> SEQUENCE: 16

cagcacatta gggagcttac acgt                                            24
```

SPECIFIC MONOCLONAL ANTIBODY AGAINST THE N ANTIGEN OF HUMAN RESPIRATORY SYNCYTIAL VIRUS (hRSV) USEFUL FOR TREATING INFECTION, DETECTION THEREOF AND DIAGNOSIS

FIELD OF THE INVENTION

The invention relates to a monoclonal antibody or fragment thereof, which recognizes the N (nucleocapsid) protein of the human respiratory syncytial virus (RSV), useful for the development of diagnostic methods for RSV infection and for the production of pharmaceutical compositions intended for the treatment, protection and/or prophylaxis of RSV infection.

BACKGROUND OF THE INVENTION

Acute respiratory tract infections are the leading cause of pediatric hospitalizations and deaths worldwide (Bryce et al., 2005). During the cold months, respiratory tract infections caused by viruses become more acute and cause an increase in the number of cases, a situation that takes on the characteristics of an epidemic outbreak. The viruses that cause these epidemics in the pediatric population are mainly human respiratory syncytial virus (hRSV), adenovirus (ADV), influenza virus, and metapneumovirus (hMPV). However, RSV is the main causative agent of acute respiratory tract infections in infants around the world, causing severe outbreaks in the winter months. According to the WHO, this virus infects 64 million people annually, of which 160,000 die. Infection by this virus causes a wide range of clinical symptoms, which can be mild, such as rhinitis or much more severe, such as pneumonia or bronchiolitis, with the most serious conditions being observed in infants, premature infants, children with congenital heart disease, and in immunosuppressed (Cabalka, 2004; Carpenter and Stenmark, 2004; Weisman, 2003). Furthermore, the infection caused by this virus is extremely frequent and recurrent, since practically 100% of children older than three years have presented at least one episode of RSV infection (Bont et al., 2002; Hall et al., 1991). Because this infection does not leave an adequate immunological memory (Bont et al., 2002), reinfections are frequent, decreasing in severity as the age of the patient increases. However, reinfected individuals act as reservoirs and are a source of contagion for children under 1 year of age, who do generate severe respiratory symptoms. In Chile, during the cold months (May-August), this virus is the cause of 70% of the acute infections of the lower respiratory tract that require hospitalization (Avendaño et al., 2003), causing the death of 0.1% of them. Although this percentage is low, the large number of cases makes the number of deaths very significant. This situation causes the saturation of emergency care services, which has often required the application of emergency measures in health services, such as the conversion of beds for pediatric patients in hospitals, the suspension of elective and scheduled surgeries. and hiring support staff during the months in which the outbreak occurs. The RSV diagnostic method that is usually used in hospital care services is a diagnostic test based on the detection of viral antigens by direct immunofluorescence of nasopharyngeal isolates. The limitation of this test refers to the need for trained personnel to process and analyze the samples and, furthermore, to the fact that the results of said test are not obtained immediately, leaving a period of time in which the patient is still It is not diagnosed, but the infection continues its course. Faced with such problems, the development of efficient monoclonal antibodies, which can be used to create alternative hRSV detection tests, which require minimal training and are quick to perform (such as immunochromatographic tests) appear as a necessary alternative to supply this need, since they allow the specific recognition of viral antigens in samples from patients infected with hRSV, also requiring a low sample quantity. In this way, the present invention translates into an antibody capable of detecting hRSV antigens in a very efficient, effective way and present in low quantities, which allows the development of an alternative method of detection and diagnosis that is fast, effective and accurate for patients infected with hRSV, in order to determine an early and adequate treatment that influences the evolution of the disease.

From a therapeutic point of view, currently the only standard solution used to prevent the potentially more serious cases of infection with hRSV in the most vulnerable population is the use of Palivizumab (Olchanski, et. Al., 2018). This is a humanized monoclonal antibody directed against another protein of hRSV, the F protein. The mechanism of action of this antibody is the neutralization of the entry of the virus to the target cell, so it requires multiple administrations during the winter period. Since this antibody recognizes a highly variable surface protein of the virus, some of the strains are not recognized by this antibody, rendering its use ineffective. As an alternative solution to this problem, the inventors have demonstrated that the anti-protein N antibody of the present invention is also effective in preventing the development of the pulmonary manifestation of infection by hRSV, which makes it possible to propose its use for the preparation of pharmaceutical compositions intended for the treatment and/or prophylaxis of hRSV infection. This new antibody has the additional advantage that the N protein (Collins et. Al, 2013) has a lower variability than that of the F protein, thus allowing the recognition of a greater number of virus strains.

DESCRIPTION OF FIGURES

In FIG. 5A) a culture of Hep-2 cells infected with $1.8\times10^5$ PFUs of hRSV expressing green fluorescent protein (GFP) is shown. The culture was maintained for 48 hours to promote replication of the hRSV and to be able to detect infected cells by means of flow cytometry when expressing the GFP protein. Subsequently, cells were fixed with 4% PFA and permeabilized with 0.2% saponin to stain intracellularly with the anti-N antibody followed by staining with secondary antibody coupled to APC. In this way, the infected cells (GFP+) and the anti-N antibody could be measured consecutively. Uninfected cells, infected cells unstained with the anti-N antibody and cells stained only with the secondary antibody were used as cytometry controls. In FIG. 5 it can be seen that all the cells infected with the hRSV (GFP+) are identified by staining with the anti-N antibody (GFP+anti-N+). The results are summarized in graph (5B).

Figure 1:
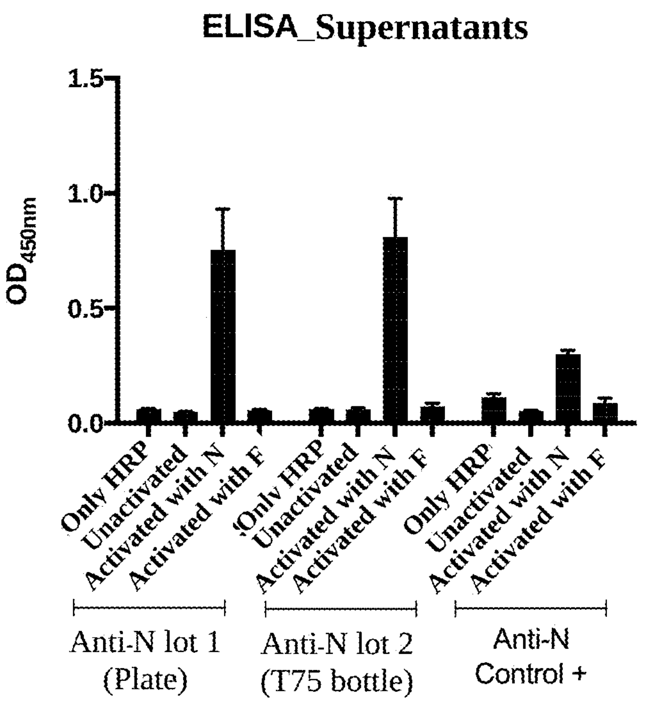
FIG. 1: Verification of the production of anti-N antibodies by the hybridoma. ELISA technique that demonstrates the affinity of the Anti-N antibody for the N protein and not for other viral proteins. To determine the activity from the supernatant of the hybridoma cultures grown by two different techniques, the specificity of the antibodies for their ligand was measured by ELISA. Shown in the figure: Anti-N batch 1=supernatant obtained from the first batch of hybridoma cells grown in a 6-well plate. Anti-N batch 2=supernatant obtained from the second batch of hybridoma cells grown in a T75 bottle and sonicated. Anti-N positive control=Monoclonal antibody that recognizes the N protein, which is used as the first positive control in this assay. Supernatants were evaluated in unactivated wells, activated with hRSV N protein, and activated with hRSV F protein. Subsequently, conjugation with a secondary antibody labeled with HRP (horseradish peroxidase) was detected, additionally a control with only the secondary antibody=Only HRP was included. The results show that the antibody of the invention, obtained with either of the two hybridoma culture methods, has a high recognition of the N protein, almost three times that of the positive control, of polyclonal anti-N antibody.

Additionally, the results of a real-time PCR that measured the viral load (6 B), animals previously immunized with the antibody of the invention on day 4 after infection with hRSV are plotted. The uninfected control=Mock is observed, the control of non-immunized animals, with virus infection=hRSV, control of animals previously immunized with the commercial anti-F protein antibody of hRSV=Palivizumab (anti F), animals previously immunized with the antibody anti-N protein of the invention=Anti-N, and Isotype control. In all cases, the antibody dose was 5 mg/kg.

DESCRIPTION OF THE INVENTION

The present invention aims at a monoclonal antibody specific for respiratory syncytial virus (RSV). Specifically, the IgG2A monoclonal antibody secreted by a hybridoma cell line generated in the laboratory, directed specifically for the viral N antigen, which is associated with the nucleocapsid of the virus. The antibody can be used for assays for the detection and/or determination of infection by hRSV. This antibody is in its pure state and free of any other contaminating biological material.

The inventors have sequenced the antibody of the invention, where the sequence of the variable region of the heavy chain is found in SEQ ID No. 1, and the nucleotide sequence that encodes it is found in SEQ ID No. 3. Additionally, the sequence of the variable region of the light chain is found in SEQ ID No. 2, and the nucleotide sequence that encodes it is found in SEQ ID No. 4. The CDRs of this antibody are found in their peptide sequences in the SEQ ID Nos. 5, 6 and 7 for the heavy chain and in SEQ ID Nos. 11, 12 and 13 for the light chain. While the nucleotide sequences that encode them are found in SEQ ID Nos. 8, 9 and 10 for the heavy chain and in SEQ ID Nos. 14, 15 and 16 for the light chain.

In one aspect of the invention, a method is provided for the prevention and treatment of infection caused by human respiratory syncytial virus (hRSV) in a given host, which comprises the administration of a composition comprising the monoclonal antibody of the invention, in sufficient doses to prevent disease. In the case of human use, the antibody can be humanized to minimize the possibility of an immune response against the host (patient) using it.

Furthermore, the invention makes it possible to provide the formulation of any pharmaceutical form of the monoclonal antibody of the invention for the treatment or prevention of the disease caused by hRSV.

The invention also provides methods for the diagnosis and detection of hRSV viral antigens in biological samples, in which the monoclonal antibody of the invention is used in assays such as: ELISA, Immunofluorescence Microscopy, Immunohistochemistry, Flow cytometry, Cell purification (Cell Sorter, by fluorescence, by association with magnetic spheres or any separation method that uses the antibody), Immunoprecipitation, Western blot and Chromatography. The samples can be in vitro cells infected with hRSV or samples obtained from individuals suspected of infection with hRSV. In the case of samples from an individual, they may correspond to nasal secretions, nasal washes, pharyngeal secretions, bronchial washes or secretions or any other type of sample that is considered appropriate. The invention provides the opportunity to develop a method of isolation and detection of respiratory syncytial virus in biological samples and cell cultures that are put in contact with the monoclonal antibody of the invention coupled to any type of solid support, such as nitrocellulose, membrane of nylon or other support. The invention presents the opportunity to develop rapid detection kits for Respiratory Syncytial Virus or similar, containing the antibody of the invention. It also provides the possibility of incorporating any type of molecule or substrate chemically linked to the monoclonal antibody of the invention, such as fluorophores, biotin, radioisotopes, metals, enzymes and/or any chemical element coupled to the aforementioned monoclonal antibodies, as a detection method, treatment, analysis and/or diagnosis in biological samples. The invention has great potential to be used as a therapeutic method, or prophylaxis for use in humans, for which it must be humanized.

Thus, the present invention relates to a monoclonal antibody of the IgG2A isotype that specifically recognizes the N protein, of the nucleocapsid of the human Respiratory Syncytial Virus (hRSV).

A monoclonal antibody is a type of homogeneous antibody that is characterized by specifically recognizing a single antigen. They are produced by a single hybrid cell (hybridoma), which is the product of the fusion of a B lymphocyte clone and a tumor plasma cell. The property of specifically binding and with high affinity to an antigen has prompted the development of monoclonal antibodies as a very useful tool for the detection of molecules that generate great scientific, clinical and industrial interest. At present, monoclonal antibodies are widely used, both in basic and applied research, due to their specificity and the reproducibility of the results obtained with them; which allows to better substantiate the investigation. However, it is in the area of biomedicine where monoclonal antibodies have had enormous practical applications, either for diagnosis and treatment of multiple infectious diseases, and as therapy for other pathologies. Although it is true that monoclonal antibodies are used in all types of detection and diagnostic techniques, it is in the design of in vitro diagnostic kits that the best results have been obtained. For this, there are currently various rapid detection kits, such as the pregnancy test, which is based on the determination of chorionic gonadotropin (hCG) levels in urine using anti hCG antibody. Furthermore, monoclonal antibodies for therapeutic use have gained great relevance. At present there are therapeutic treatments for different pathologies, through the use of commercial monoclonal antibodies such as: Alemtuzumad, Gemtuzumab ozogamicin, Rituximab, Trastumab, etc.

hRSV is an enveloped RNA virus that belongs to the Paramyxoviridae family, Pneumovirinae subfamily (Alfonso et. Al, 2016). Its RNA is transcribed into 10 mRNAs, each of which encodes a viral protein, with the exception of M2 mRNA, which has two 22 nucleotides overlapping open reading frames (ORFs) that encode two different proteins M2-1 and M2-2. The proteins encoded by the other mRNAs are nucleoprotein (N), phosphoprotein (P), L protein, matrix protein (M), NS1, NS2, SH, fusion protein (F) and G (Collins et. Al., 2013). The N protein associates with genomic RNA forming the nucleocapsid, L is a nucleocapsid-associated RNA polymerase, P interacts with N and L, M is a non-glycosylated protein found on the inner face of the viral envelope, NS1 and NS2 are non-structural proteins, and SH, G, and F are part of the viral envelope. The RSV diagnostic kits developed so far use antibodies against the F, N and/or G proteins of RSV, and the antibodies suggested for the treatment or prophylaxis of RSV infection are also directed at the F, M2 and G proteins (CL948-96, CN101130765, U.S. Pat. No. 6,790,611, WO2009088159, Munoz-Durango et. Al., 2018).

N is a 44 Kd molecular weight polypeptide that belongs to the nucleocapsid of the Virus together with the P and L protein. Recent research indicates that this N protein would be interfering with the function of cells of the immune system—specifically dendritic cells and T lymphocytes-, (Céspedes P F et al. 2014). This finding allows us to suppose that this antigen can be considered as a target for new antiviral therapies.

From the investigations carried out for the present invention, related to the effects that viral antigens derived from human Respiratory Syncytial Virus (hRSV) have on the immune system; Specific murine monoclonal antibodies were generated for the detection of RSV antigens that have advantages over those commercially available. Specifically, the monoclonal antibody produced by the hybridoma generated in the inventors' laboratory was found to be very useful for determining hRSV infection in both in vitro and in vivo immunological assays using various detection techniques. Due to this, said antibodies provide a valuable tool for detection, diagnosis and/or therapy of infection caused by human Respiratory Syncytial Virus. The monoclonal antibody of the invention can have multiple applications for diagnostic and therapeutic use, such as its use in immunoblot techniques, immunofluorescence, immunochromatography, flow cytometry, production of pharmaceutical forms that comprise it, or any other that involves its use, including for human use. The antibody can be linked to a marker that allows its detection. Examples of possible markers correspond to fluorophores, biotin, radioisotopes, metals, enzymes and any other type of appropriate marker for antibodies.

The monoclonal antibody of the invention can be found in its natural form, as secreted by the hybridoma, or also as antigen-binding fragments. Antigen-binding fragments are fragments of the antibody capable of binding antigen, such as Fab or Fab' fragments. In the present application, the applications of the antibody of the invention, while mentioning the use of the antibody, also include the use of anti-N monoclonal antibody binding fragments. Furthermore, in the case of the generation of compositions comprising the antibody of the invention, said compositions may comprise the murine antibody or the humanized or chimeric antibody of the invention. This is especially useful in compositions for human administration, as a way to minimize the possibility that the immune system of the individual treated with the composition will generate a response against the antibodies of the invention.

In this way, the invention refers to a monoclonal antibody or a fragment of this that binds to the nucleoprotein N protein of the human respiratory syncytial virus (hRSV) where said antibody has a variable region of the heavy chain with at least 95%, 96%, 97%, 98%, 99% or 100% identity with SEQ ID No: 1 and has a light chain variable region with at least 95%, 96%, 97%, 98%, 99% or 100% identity with SEQ ID No: 2. Likewise, the invention can also be defined as a monoclonal antibody or a fragment thereof that binds to the RSV nucleoprotein N protein, in which its heavy chain variable region is encoded in a nucleotide sequence that has at least 90%, 91%, 92%, 93%, 94%, 95%, 96%, 97%, 98%, 99% or 100% identity with SEQ ID No: 3 and its respective complementary reverse sequence and its variable region light chain is encoded in a nucleotide sequence that has at least 90%, 91%, 92%, 93%, 94%, 95%, 96%, 97%, 98%, 99%, or 100% identity with SEQ ID No: 4.

In a preferred embodiment, the antibody of the invention, which binds to the nucleoprotein N protein of the human respiratory syncytial virus (hRSV) has a variable region of the heavy chain whose CDR1, CDR2 and CDR3 are encoded by sequences that have at least a 95%, 96%, 97%, 98%, 99% or 100% identity with SEQ ID No:8, SEQ ID No:9 and SEQ ID No:10, respectively, and has a light chain variable region whose CDR1, CDR2 and CDR3 are encoded by sequences that have at least a 95%, 96%, 97%, 98%, 99% or 100% identity with SEQ ID No:14, SEQ ID No:15 and SEQ ID No:16 respectively.

In a preferred embodiment, the antibody of the invention, which binds to the nucleoprotein N protein of the human respiratory syncytial virus (hRSV) has a variable region of the heavy chain whose CDR1, CDR2 and CDR3 have amino acid sequences with at least a 95%, 96%, 97%, 98%, 99% or 100% identity with SEQ ID No:5, SEQ ID No:6 and SEQ ID No:7, respectively, and at the same time has a variable region of the chain light whose CDR1, CDR2 and CDR3 have amino acid sequences with at least a 95%, 96%, 97%, 98%, 99% or 100% identity with SEQ ID No:11, SEQ ID No:12 and SEQ ID No:13, respectively.

It will be apparent to the person skilled in the art that the monoclonal antibody or its functional fragment, which binds to the nucleoprotein N protein of hRSV, can be modified in the regions adjacent to the variable regions to obtain a chimeric antibody, especially a humanized antibody. Where the specificity of said chimeric or humanized antibody is given by the variable regions, as defined in the previous paragraph, that is, a variable region of the heavy chain with at least 95% identity with SEQ ID No: 1 and a light chain variable region with at least 95% identity to SEQ ID No: 2.

In one embodiment, the invention provides a pharmaceutical composition for the treatment and/or prophylaxis of infection caused by RSV where this composition comprises the monoclonal antibody or a fragment of this that binds to the nucleoprotein N protein of RSV as defined, that is, it has a heavy chain variable region with at least a 95% identity with SEQ ID No: 1 and has a light chain variable region with at least a 95% identity with SEQ ID No: 2 and a pharmaceutically acceptable carrier.

In another embodiment, the invention provides a method for detecting human respiratory syncytial virus in a sample, which comprises contacting the sample with the monoclonal antibody or a fragment of this that binds to the nucleoprotein N protein of hRSV as defined, that is, it has a heavy chain variable region with at least a 95% identity with SEQ ID No: 1 and has a light chain variable region with at least a 95% identity with SEQ ID No: 2 and detecting the binding of the antibody to the antigen. Where the technique used to detect the binding of the antibody with the antigen corresponds to ELISA, immunofluorescence, immunohistochemistry, immunochromatography, flow cytometry, cell sorter, immunoprecipitation, Western blot, or any other available in the art. Alternatively, the antibody or fragment thereof, as defined, that is, has a heavy chain variable region with at least a 95% identity to SEQ ID No: 1 and has a light chain variable region with at least a 95% identity with SEQ ID No: 2, is conjugated with a marker that allows its detection. Where said marker is selected from the group consisting of fluorophores, biotin, radioisotopes, metals, enzymes or any other marker available in the art.

In one embodiment, the antibody or fragment thereof as defined, that is, it has a heavy chain variable region with at least a 95% identity to SEQ ID No: 1 and has a light chain variable region with at least a 95% identity with SEQ ID No: 2, is immobilized on a solid support. Where said solid support is chosen from nitrocellulose, cellulose, polyethylene, nylon, or any other appropriate support available in the art.

Finally, the invention also aims at a method of treatment or prophylaxis of a syncytial virus infection which comprises administering to an animal or a human being, a pharmaceutical composition comprising the monoclonal antibody or a fragment of this that binds to the RSV nucleoprotein N protein that has a heavy chain variable region with at least a 95% identity to SEQ ID No: 1 and has a light chain variable region with at least a 95% identity to SEQ ID No: 2 and a pharmaceutically acceptable carrier. In a preferred embodiment, this pharmaceutical composition is administered intramuscularly.

Examples are described below that allow the demonstration of different applications of the monoclonal antibody of the invention.

Example 1: Obtaining the Antibody of the Invention

The inventors obtained the secretory hybridoma of the anti-N monoclonal antibody. This hybridoma was cultured for about one month and a stable culture of the cells was obtained. From this stable culture, multiple aliquots corresponding to stocks stored at −150° C. were generated. The antibody of the invention was sequenced, and the sequences are disclosed in this patent. The sequence of the variable region of the heavy chain is found in SEQ ID No: 1, and the nucleotide sequence that encodes it is found in SEQ ID No: 3. Additionally, the sequence of the variable region of the light chain is found in SEQ ID No: 2, and the nucleotide sequence that encodes it is found in SEQ ID No: 4.

Figure 2:
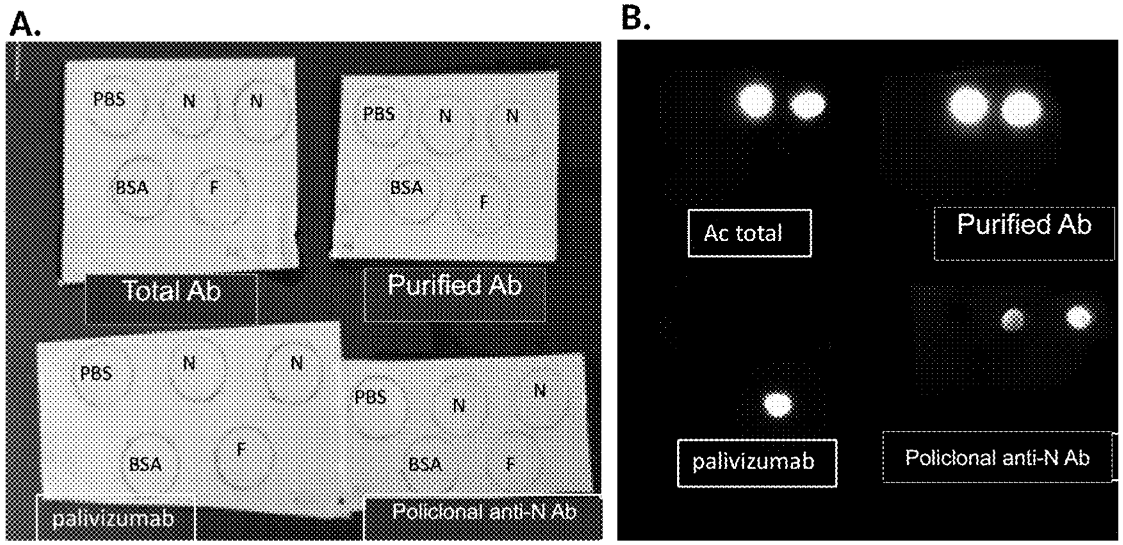
FIG. 2: Evaluation of the specificity of the anti-N monoclonal antibody for the N protein by means of the dot blot technique. The image represents the specificity of the Antibody for RSV N antigen, through a Dot blot assay. (A) It is shown with which protein each circle of the membrane was sensitized. Each membrane was impregnated with 5 proteins in 5 points. PBS and BSA were used as vehicle controls, the F protein of hVRS was used as a specificity control and as a positive control of the technique, and finally two points with protein N as Antigen. (B) Image obtained after 5 minutes of exposure with total Ab, corresponds to the supernatant of the hybridoma before purifying it. Purified Ab, which is the Anti-N antibody of the invention, the commercial antibody Palivizumab that recognizes the F protein, and polyclonal anti-N antibody The results show that the antibody of the invention both in the total supernatant, as well as purified, strongly and specifically recognizes the N protein of hVRS.

Example 2: RSV Antigen Detection Assay, Anti-N Monoclonal Antibody Specificity for Purified RSV Antigens An ELISA was performed to verify that the antibodies secreted by the hybridoma cells recognize the N protein of the hRSV. The plate was sensitized with N and F protein to evaluate the specificity of the antibody, as a control an inactivated plate was used, and plates with only the secondary antibody were also evaluated. As can be seen in FIG. 1, the antibodies of the invention, evaluated as the supernatants of the hybridomas (lot 1 and lot 2) are able to recognize only the N protein and do not recognize the F protein, which suggests a high Specificity of the antibody for the N protein. As indicated in the description of the figures, the antibody of the invention has a high recognition rate for the N protein, almost three times that of the positive control, polyclonal anti-N antibody. A second test was performed to evaluate the specificity of the antibody of the invention, using the dot blot technique. Each membrane was sensitized with hRSV N protein in 2 spots, 2 negative controls (PBS [phosphate buffer saline] and BSA [bovine serum albumin]) and RSV F protein. The results are shown in FIG. 2, the supernatant of the complete hybridoma (total Ab), the purified antibody of the invention (purified Ab), Palivizumab®, which recognized RSV F protein, and a polyclonal antibody against RSV N protein were evaluated. The results show that the antibody of the invention both in the total and purified supernatant strongly and specifically recognizes the N protein of hRSV.

Figure 3:
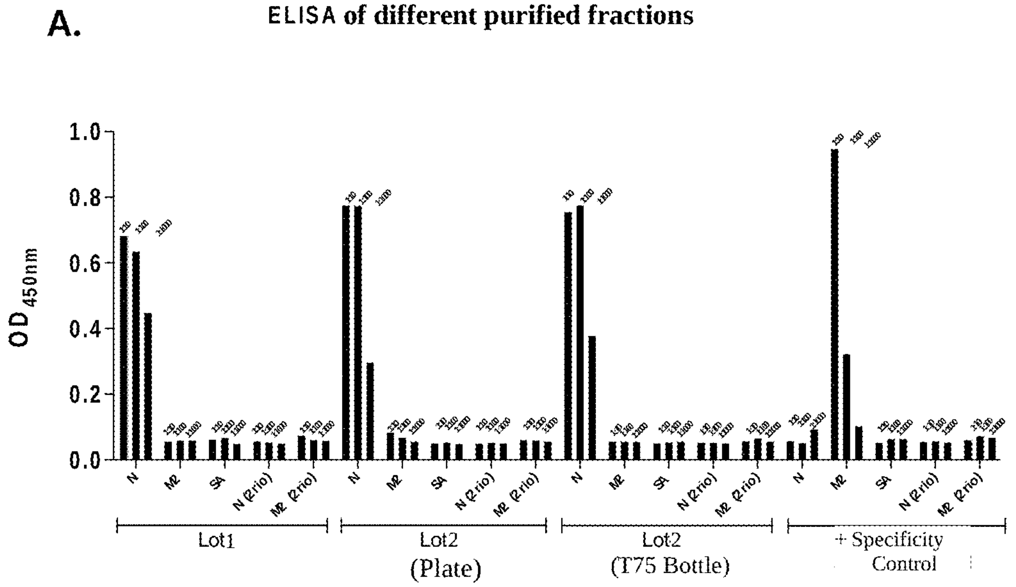
FIG. 3: Establishment of ELISA as a technique that allows the verification of the production of anti-N antibody between batches, in addition to corroborating its specificity and sensitivity. In A the results of an ELISA of the fractions of purified hybridoma supernatants in different assays are shown. Lot 1 is a first purification. Lot 2 corresponds to a purification carried out later, which was made from the supernatant obtained from a plate culture of 6 (Lot 2 plate) and from a T75 bottle (Lot 2 bottle). The Positive Specificity Control corresponds to an anti-M2 antibody that recognizes the viral M2 protein. Wells were activated with hVRS N and M2 proteins. SA=wells not activated. N (2nd) and M (2nd) correspond to activated wells where the primary antibody was not added. On the other hand, in B, serial dilutions of a purified fraction of the anti-N antibody of the invention are shown, in order to achieve the detection limit dilution of the N protein. This assay also evaluates the specificity of the anti-N antibody by not seeing reactivity against other hRSV proteins such as F, as well as in the non-activated (SA) wells or in which the primary antibody N (2rio) and F (2rio) were not added. As a negative control, another antibody of the same IgG2A Isotype was used that does not recognize the N protein (Isotype) and as a specificity control, Palivizumab was used, which recognized the F protein.
Figure 3:
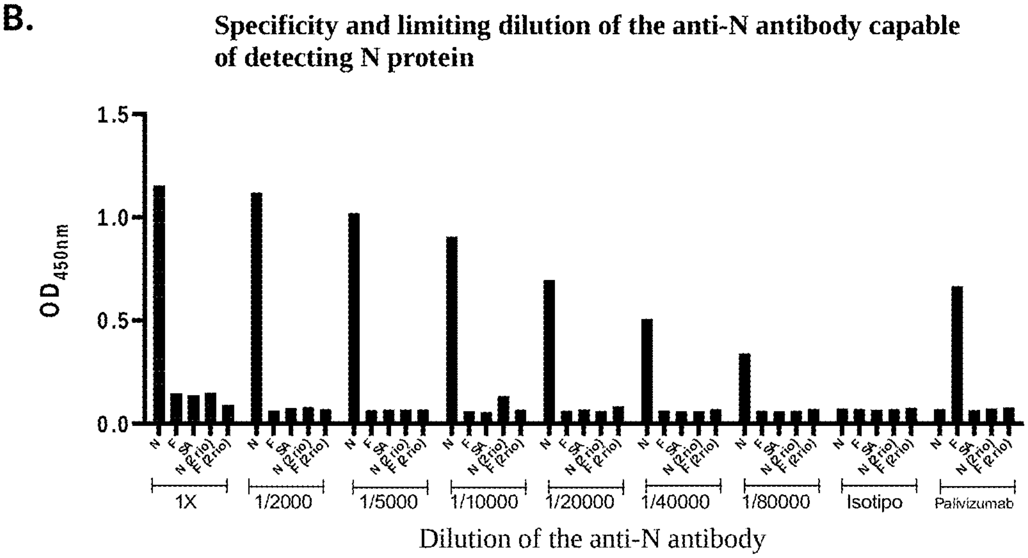

Example 3: Assay to Determine the Efficiency and Specificity of the Monoclonal Antibody to Detect Viral Antigens After determining that the purified antibody recognizes the N protein of the hRSV, an ELISA was performed to ensure its specificity. In this ELISA, different concentrations of the primary antibodies were used and the concentration of the N protein was kept constant (50 ng). An α-M2 antibody that is directed against the viral protein M2 and a commercial anti-F antibody that is directed against the viral F protein was used as a specificity control. FIG. 3A shows that the antibody is capable of binding to the N protein, no signal observed in wells activated with protein M2 or without activation (SA). The antibodies of the invention were evaluated from 2 different productions, Lot 1 is a first purification. Lot 2 corresponds to a purification carried out later, where a hybridoma culture was simultaneously performed in a plate and in a T75 bottle. The results show a high efficiency of the Antibody of the invention in detecting the RSV N protein, without significant differences between the different purifications tested. From a purified and concentrated fraction of the anti-N antibody, dilutions from 1/2000 were made to determine the minimum amount of anti-N antibody capable of recognizing the N protein. As shown in FIG. 3B, again determined the ability of the anti-N antibody to bind to N protein, with no signal being observed in wells activated with F protein or non-activated (SA). The results show that even at the lowest concentration studied, 1/80000, the antibody of the invention makes it possible to detect the presence of hRSV N protein.

Example 4. Sensitivity of Anti-N Monoclonal Antibody to RSV Antigens

Figure 4:
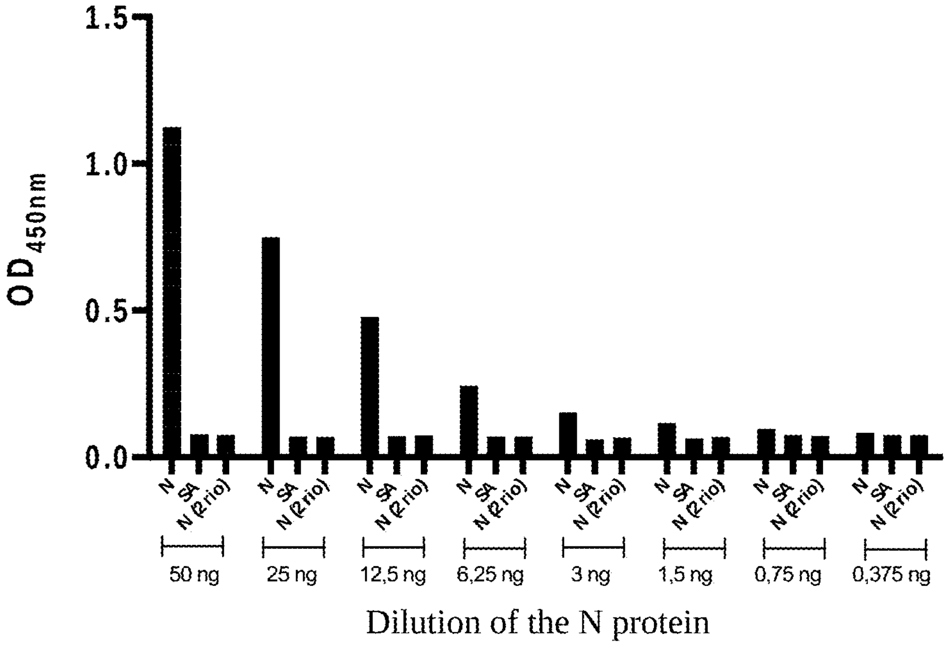
FIG. 4: Evaluation of the minimum concentration of N protein detected by the anti-N antibody. The figure corresponds to the results of an ELISA performed with wells activated with serial dilutions of the N protein of hRSV, starting from 50 ng to 0.375 ng and at a constant dilution of the anti-N antibody of the invention (1/5000). In this ELISA the technical controls of wells not activated (SA) and activated with the N protein, but only revealed with the secondary antibody [N (2rio)] were included. The results show that the antibody is able to reliably recognize from 6.25 ng of N protein.

In order to determine the minimum amount of N protein that the anti-N antibody of the invention was capable of detecting (analytical sensitivity), serial dilutions of protein N were made, starting from 50 ng to 0.375 ng. Then, by means of the ELISA technique and at a constant dilution of the anti-N antibody (1/5000) it was determined that the antibody is capable of reliably recognizing up to 6.25 ng of N protein, as shown in FIG. 4.

Figure 5:
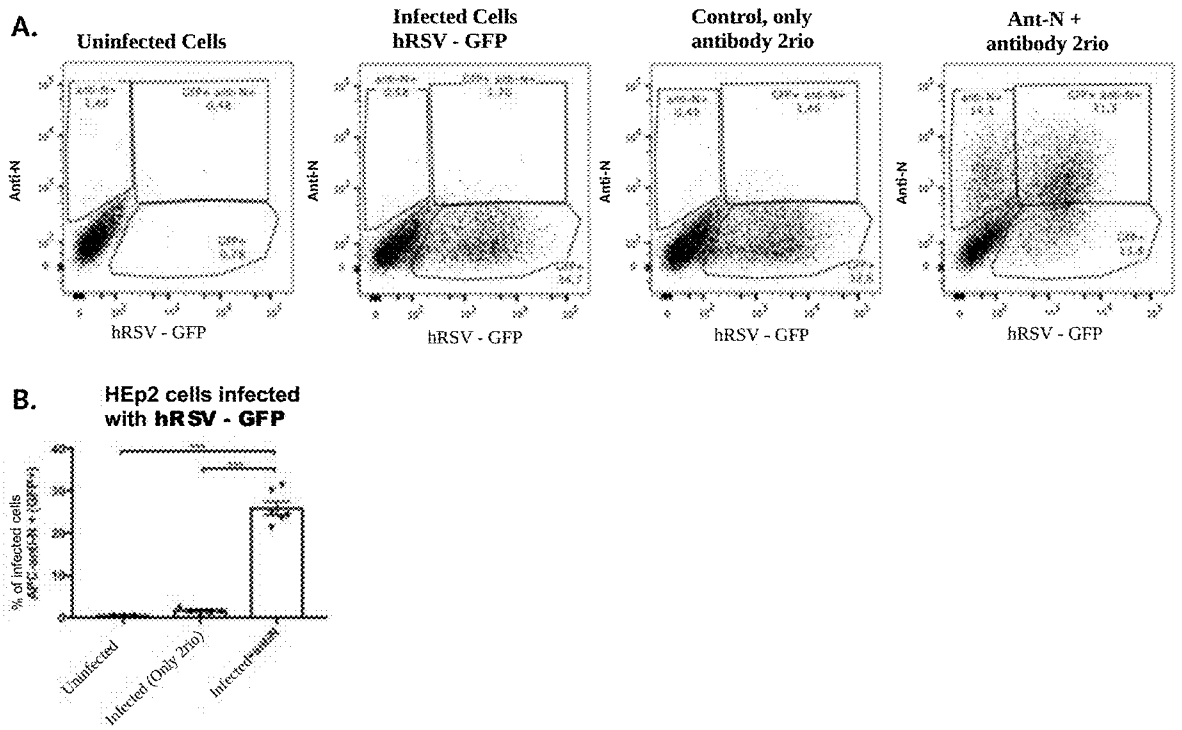
FIG. 5: Capacity of the anti-N antibody to detect cells infected with hRSV by the flow cytometry technique.

Example 5. Detection of Human Cells Infected with RSV, by Flow Cytometry, Using the Anti-N Antibody To evaluate the ability of the anti-N antibody to detect human cells infected with HRV, the Hep-2 cell line corresponding to a human carcinoma epithelium was used. These cells were infected in vitro for 2 hours with $1.8\times10^4$ PFU of the hRSV that expresses the green fluorescent protein (GFP) when the virus replicates. The culture was maintained for 48 hours to promote replication of the hRSV and to be able to detect infected cells by means of flow cytometry when expressing the GFP protein. Additionally, these cells were fixed with 4% PFA and permeabilized with 0.2% saponin to stain intracellularly with the anti-N antibody. After 30 minutes of incubation with the anti-N antibody, the cells were washed and incubated with a secondary antibody coupled to allophycocyanin (APC). In this way, the infected cells (GFP+) and the anti-N antibody could be measured consecutively. Uninfected cells, infected cells unstained with the anti-N antibody and cells stained only with the secondary antibody were used as cytometry controls. In FIG. 5A it can be seen that all cells infected with the hRSV (GFP+) are identified by staining with the anti-N antibody (GFP+anti-N+). Furthermore, when quantifying the data obtained in flow cytometry, it can be concluded that the anti-N antibody is capable of specifically discriminating infected cells (FIG. 5B).

Figure 6:
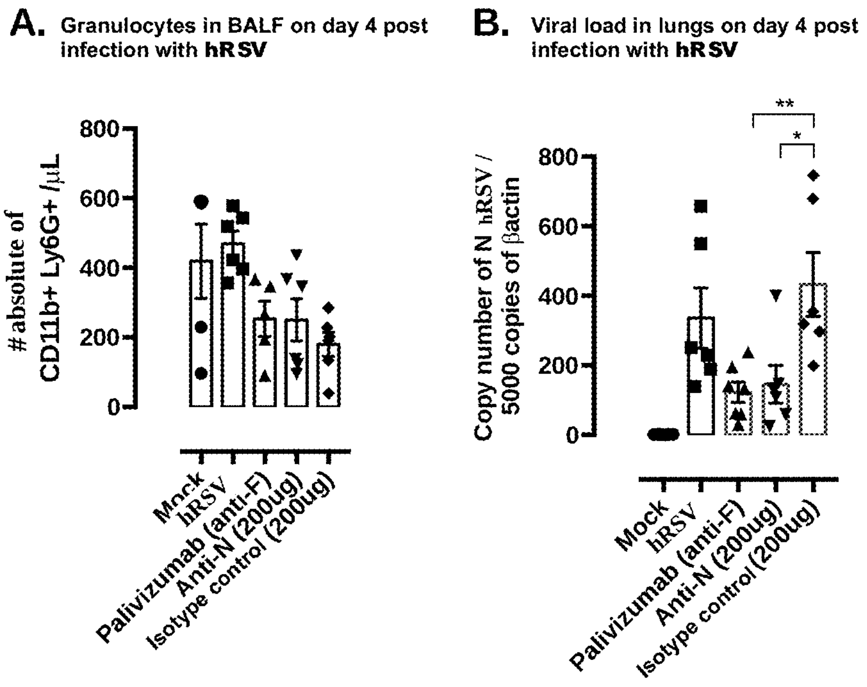
FIG. 6: Evaluation of the therapeutic capacity of the anti-N antibody in pre-clinical models. The results of a flow cytometry assay in which the number of infiltrating neutrophilic granulocytes in the lung (6 A) in the bronchioalveolar lavage fluid (BALF) of animals previously immunized with the antibody of the invention were graphed on day 4 post infection with hRSV. The uninfected control=Mock is observed, the control of non-immunized animals, with virus infection=hRSV, control of animals previously immunized with the commercial anti-F protein antibody of hRSV=Palivizumab (anti F), animals previously immunized with the antibody of the invention=Anti-N, and Isotype control, that is to say another antibody of the same Isotype, IgG2A, that does not recognize the N protein.

Example 6: Evaluation of the Prophylactic Effect of the Antibody of the Invention in a RSV Infection To evaluate the ability of the antibody of the invention to prevent the disease or at least reduce its effects in the patient, a dose of 5 mg/kg (approximately ug per animal) of anti-N monoclonal antibody was administered to BALB/c mice. Controls were performed by administering Palivizumab and Isotype control to another group of BALB/c mice. The day after passive immunization, these animals plus an unimmunized control group were infected with hRSV, on the fourth day post infection the test was ended and the number of infiltrating neutrophils in the bronchioalveolar lavage was measured, a parameter associated with the severity of the disease. The results are shown in FIG. 6A. It can be seen that immunization with the antibody of the invention decreases the infiltrate of neutrophils at the pulmonary level to levels similar to those achieved with the Palivizumab control. An additional clinical parameter that is important to measure to determine the severity of the disease is the quantification of the viral load in the lungs of infected mice. To determine the viral load, RNA is obtained from the lungs of the mice and from these a real-time PCR is performed to quantify the expression of the virus genes, in this case the expression of the nucleoprotein gene (N). According to the results shown in FIG. 6B, the N anti-body of the invention is capable of reducing the pulmonary viral load, in an infection by hRSV, in a proportion equivalent to that achieved by the commercial anti-F protein antibody of hRSV, Palivizumab These examples demonstrate the specificity of the antibody of the invention, as well as its utility both in virus detection, and therefore for the development of RSV infection diagnostic methods; and in the neutralization thereof, and therefore for the production of pharmaceutical compositions intended for the treatment, protection and/or prophylaxis of RSV infection.

REFERENCES

1. Bryce J, Boschi-Pinto C, Shibuya K, Black R E; WHO Child Health Epidemiology Reference Group. WHO estimates of the causes of death in children. Lancet. 2005 Mar. 26-Apr. 1; 365(9465):1147-52.
2. Cabalka A K. Physiologic risk factors for respiratory viral infections and immunoprophylaxis for respiratory syncytial virus in young children with congenital heart disease. Pediatr Infect Dis J. 2004 January; 23(1 Suppl):S41-5.
3. Carpenter T C, Stenmark K R. Predisposition of infants with chronic lung disease to respiratory syncytial virus-induced respiratory failure: a vascular hypothesis. Pediatr Infect Dis J. 2004 January; 23(1 Suppl):S33-40.
4. Weisman L. Populations at risk for developing respiratory syncytial virus and risk factors for respiratory syncytial virus severity: infants with predisposing conditions. Pediatr Infect Dis J. 2003 February; 22(2 Suppl):S33-7; discussion S37-9.
5. Louis Bont, Paul A. Checchia, Brigitte Fauroux, Josep Figueras-Aloy, Paolo Manzoni, Bosco Paes, Eric A. F. Simões, and Xavier Carbonell-Estrany. Defining the Epidemiology and Burden of Severe Respiratory Syncytial Virus Infection Among Infants and Children in Western Countries. Infect Dis Ther. 2016 September; 5(3): 271-298. Published online 2016 Aug. 1. doi: 10.1007/s40121-016-0123-0
6. Hall C B, Walsh E E, Long C E, Schnabel K C. Immunity to and frequency of reinfection with respiratory syncytial virus. J Infect Dis. 1991 April; 163(4):693-8.
7. Luis F. Avendaño, Maria Angelica Palomino and Carmen Larrañaga. Surveillance for Respiratory Syncytial Virus in Infants Hospitalized for Acute Lower Respiratory Infection in Chile (1989 to 2000). J Clin Microbiol. 2003 October; 41(10): 4879-4882. doi: 10.1128/JCM.41.10.4879-4882.2003
8. Collins P L, Fearns R, Graham B S. Respiratory syncytial virus: virology, reverse genetics, and pathogenesis of disease. Curr Top Microbiol Immunol 2013; 372:3-38. Available from http://link.springer.com/10.1007/978-3-64.2-38919-1
9. Natalia Olchanski, Ryan N Hansen, Elle Pope, Brittany D'Cruz, Jaime Fergie, Mitchell Goldstein, Leonard R Krilov, Kimmie K McLaurin, Barbara Nabrit-Stephens, Gerald Oster, Kenneth Schaecher, Fadia T Shaya, Peter J Neumann and Sean D Sullivan. Palivizumab Prophylaxis for Respiratory Syncytial Virus: Examining the Evidence Around Value Open Forum Infect Dis. 2018 March; 5(3): ofy031. Published online 2018 Feb. 7. doi: 10.1093/ofid/ofy031
10. Alfonso C L, Amarasinghe G K, Bányai K, et al. Taxonomy of the order Mononegavirales: update 2016. Arch Virol. 2016; 161:2351-2360. Available from: http://link.springer.com/10.1007/s00705-016-2880-1
11. Natalia Muñoz-Durango, Magdalena S. Pizarro-Ortega, Emma Rey-Jurado, Fabián E. Díaz, Susan M. Bueno and Alexis M. Kalergis. Patterns of antibody response during natural hRSV infection: insights for the development of new antibody-based therapies. https://doi.org/10.1080/13543784.2018.1511699
12. Céspedes P., Bueno S M, Ramírez B A, Gomez R S, Riquelme S A, Palavecino C E, Mackem-Oberti J P, Mora J E, Depoil D, Sacristán C, Cammer M, Creneguy A, Nguyen T H, Riedel C A, Dustin M L and Kalergis A M. Surface expression of the hRSV nucleoprotein impairs immunological synapse formation with T cells. Proc Natl Acad Sci USA. 2014 Aug. 5; 111(31):E3214-23. doi:

The invention claimed is:

1. A monoclonal antibody or a fragment thereof that binds to a nucleoprotein protein N of a human respiratory syncytial virus (RSV), wherein said antibody or fragment thereof has a variable region of a heavy chain whose CDR1, CDR2 and CDR3 have amino acid sequences comprising the amino acid sequence SEQ ID No:5, SEQ ID No:6, and SEQ ID No: 7, respectively, and at the same time has a variable region of a light chain whose CDR1, CDR2, and CDR3 have amino acid sequences comprising the amino acid sequence SEQ ID No: 11, SEQ ID No: 12, and SEQ ID No: 13, respectively.

2. The monoclonal antibody or a fragment thereof that binds to the nucleoprotein protein N of RSV according to claim 1, wherein the antibody has a variable region of the heavy chain whose CDR1, CDR2, and CDR3 are encoded by sequences comprising the nucleic acid sequence SEQ ID No:8, SEQ ID No:9, and SEQ ID No: 10, respectively, and their respective complementary reverse sequences and has a variable region of the light chain whose CDR1, CDR2, and CDR3 are encoded by sequences comprising the nucleic acid sequence SEQ ID No:14, SEQ ID No: 15, and SEQ ID No: 16, respectively, and their respective complementary reverse sequences.

3. The monoclonal antibody or a fragment thereof that binds to the nucleoprotein protein N of RSV according to claim 1, wherein the antibody is a humanized or chimeric antibody.

4. A pharmaceutical composition for a treatment and/or a prophylaxis of infection caused by a human respiratory syncytial virus (RSV), wherein the composition comprises the monoclonal antibody or a fragment thereof that binds to the nucleoprotein protein N of RSV of claim 1 and a pharmaceutically acceptable carrier.

5. A method for detection of human respiratory syncytial virus (RSV) in a sample, comprising contacting the sample with the monoclonal antibody or a fragment thereof that binds to the nucleoprotein protein N of RSV of claim 1; and detecting a binding of the antibody to the antigen.

6. The method according to claim 5, wherein the method used to detect the binding of the antibody to the antigen is selected from the group consisting of ELISA, immunofluorescence, immunohistochemistry, immunochromatography, flow cytometry, cell sorter, immunoprecipitation, and Western blot.

7. A method for detection of human respiratory syncytial virus (RSV) in a sample, comprising:

contacting the sample with a monoclonal antibody or a fragment thereof that binds to a nucleoprotein protein N of RSV; and detecting the binding of the antibody to the antigen, wherein the monoclonal antibody or a fragment thereof is the monoclonal antibody or a fragment thereof according to claim 1 and is conjugated with a marker which allows its detection.

8. The method according to claim 7, wherein the antibody or a fragment thereof is conjugated with a marker selected from the group consisting of fluorophores, biotin, radioisotopes, metals, and enzymes.

9. The method according to claim 8, wherein the antibody or a fragment thereof is immobilized on a solid support.

10. The method according to claim 9, wherein a material of the solid support is selected from the group consisting of nitrocellulose, cellulose, polyethylene, and nylon.

11. A method of treatment or prophylaxis of human respiratory syncytial virus (RSV) and development of a disease caused by the virus, in a subject exposed to the virus, comprising administering the pharmaceutical composition of claim 4 to the subject.

12. The method of claim 11, wherein the composition is administered intramuscularly.

* * * * *